United States Patent [19]

Flork et al.

[11] Patent Number: 4,593,045

[45] Date of Patent: Jun. 3, 1986

[54] N-ACETYL-L-ASPARTYL TAURINE USEFUL AS HYPERTENSIVE AGENT

[75] Inventors: Michel Flork, Pontaumur; Alphonse Bigou, Paris, both of France

[73] Assignee: Societe a Responsabilite Limite dite: B.F.B. Estudes et Recherches Experimentales, Paris, France

[21] Appl. No.: 600,506

[22] Filed: Apr. 16, 1984

Related U.S. Application Data

[63] Continuation-in-part of Ser. No. 400,181, Jul. 20, 1982, abandoned.

[51] Int. Cl.$^4$ .............................................. A61K 31/19
[52] U.S. Cl. ................................................... 514/562
[58] Field of Search ......................... 424/319; 514/562

[56] References Cited

U.S. PATENT DOCUMENTS

| | | | |
|---|---|---|---|
| 4,110,441 | 8/1978 | Feuer et al. | 424/211 |
| 4,324,743 | 4/1982 | Feuer et al. | 260/513 N |

OTHER PUBLICATIONS

Lahdesmaki, CA. 97:69874h.

*Primary Examiner*—Jane T. Fan
*Attorney, Agent, or Firm*—Ladas & Parry

[57] ABSTRACT

The present invention relates to N-acyl-L-aspartyl taurines and to pharmaceutical compositions containing same as active ingredient. In particular, N-acyl-L-aspartyl-taurine is useful in human or animal patients as active agent in drugs with hypotensive and/or antihypertensive effect. The product may be administered orally at a rate of 0.5 to 1.5 g per day.

4 Claims, No Drawings

N-ACETYL-L-ASPARTYL TAURINE USEFUL AS HYPERTENSIVE AGENT

This application is a continuation-in-part of Ser. No. 400,181, filed July 20, 1982, now abandoned.

The present invention relates to N-acyl-L-aspartyl-taurines and to the drugs containing said products.

Taurine (2-amino ethane sulfonic acid) is an amino acid which appears to perform an important role in the biological mechanisms. It has recently been mentioned that taurine could have interesting pharmacological properties, particularly neurotransmitter effects (it apparently acts as neurotransmission modulator), effects regulating ion transmissions through the cellular membranes, trophic effects, with the result that the use of taurine has been envisaged as anti-epileptic agent, as anti-arrythmic agent and for the treatment of hypertension. However, it is very difficult at present effectively to use taurine and its known derivatives as drugs, as a means has not yet been found for attaining a local concentration of taurine sufficient for this amino acid to have a decisive action. This is the purpose of the invention.

It has been found that by bonding taurine (or one of its salts) to the N-acyl-L-aspartyl radical, this radical performed the role of a vector capable of conveying the taurine up to the organ where its mode of action is desired (said organ most probably being the central nervous system), thus enabling this organ to benefit from the effects of a sufficient concentration maintained for a sufficient period of time.

An N-acyl-L-aspartyl and more precisely N-acetyl-L-aspartyl is used according to the invention as vector.

An N-acyl-L-aspartyl taurine and more particularly N-acetyl-L-aspartyl taurine may be prepared by reacting, towards 0° C., substantially equimolecular quantities of taurine (in basic aqueous solution) and of anhydride of N-acetyl-aspartic acid.

The product obtained possesses remarkable pharmacological properties, making of it an active ingredient which may be used in cardiology (antiarrythmic and antianginal), in neurology (anti-epileptic and minor tranquilizer), in ophthalmology (positive action on certain receptors of the retina), in nutrition (tissue growth factor and enteral food) and especially as antihypertensive drug.

The antihypertensive effect of the product according to the invention was demonstrated by the results obtained during tests made on the spontaneously hypertensive rat (SHR) and on the dog. These results are given hereinafter.

TESTS CARRIED OUT ON THE RAT (SHR)

It was known that the enrichment with taurine of the diet of the spontaneously hypertensive young rat was capable of blocking or braking hypertension. Furthermore, it has been shown that the intracerebroventricular administration of taurine was capable of lowering the arterial pressure of the spontaneously hypertensive rat but that this action was not found during systemic administration of this molecule.

It was necessary to know whether a suitably vectorized taurine would be capable of a positive action on hypertension.

The tests were carried out on rats (SHR) of 19 weeks, whose hypertension was already virtually stable, but still tended to increase slightly (about, on average, 10 mmHg in 45 days in the controls).

The arterial pressure was measured by non-sanguinary method (Narco Physiograph MK III apparatus) in the tail of the alert rat; the measurements were made on 15 rats divided into 3 batches: one batch treated daily by the i.p. route with 150 mg.kg$^{-1}$ of taurine or with the molar equivalent of vectorized taurine in aqueous solution. The control animals received the same volume (1 ml/100 g) of NaCl solute at 9 p. 1000.

Two series of experiments were carried out: one over 7 days during which the arterial pressures were measured 2 hrs., 6 hrs., 24 hrs. and 7 days aftr the last injection; the other over 14 days during which the arterial pressures were measured 6 hrs., 24 hrs., and 7 days after the last injection.

The first experimentation carried out with a treatment of seven days did not appear to contribute any formal arguments concerning the possibility of an antihypertensive effect of the vectorized taurine. Nonetheless it revealed a beneficial action of inhibition of the development of the hypertension.

The second experimentation carried out with a treatment of 14 days is much richer in information. It demonstrates a hypotensive and/or antihypertensive action. This effect is of central origin since it is not observed when the treatment is constituted by non-vectorized taurine. Furthermore, this notion is confirmed by the fact that the hypotension persists for 24 hours. The reality of the hypotensive effect is confirmed by the return of the arterial pressure to "normal" seven days (or earlier) after interruption of the treatment.

A comparison of the figures obtained 6 hrs. or 24 hrs. after the 14th administration of the different treatment shows that a highly significant drop exists in the rats treated with the vectorized taurine, but not in the other rats. Seven days later, this drop in pressure is no longer found and the arterial pressure of these animals does not differ significantly from that of the control animals nor from that of the animals treated with taurine.

In total, the hypotensive (or antihypertensive) effect of the vectorized taurine is in favour of the intervention, on the central nervous system, of taurine as agent for the physiological control of the regulation of the arterial pressure. This notion appears to be of major interest as it seems to open up a new path in the treatment or prophylaxis of the hypertension and therefore merits extensive study.

TESTS MADE ON THE DOG

Dogs weighing between 13 and 25 kg were anaesthetized with pentobarbital (30 mg/kg I.V.); the parameters measured were: arterial pressure (radial artery), cardiac frequency, femoral flowrate (electromagnetic flowmeter), vertebral flowrate and cardiac output. The total peripheral resistance, the femoral resistance and the systolic work were calculated from the preceding measurements.

The products were administered at equimolar doses, by the venous route, n=6 dogs for each product: N-acetyl-aspartyl-taurine: 12.5-25-50-100 and 200 mg/kg. Acetyl-asparate (alone): 7.65-15.28-30.57-61,14 and 122.28 mg/kg. Taurine: 4.86-9.72-19.43-38.86-77.72 mg/kg.

The haemodynamic effect of N-acetylaspartyl-taurine was therefore confronted with that of each of its constituents.

Before and after each administration, the vascular reactivity to noradrenaline (2 mcg/kg I.V.) was checked.

The results obtained for the various measurements made may be summarized as follows:

1. Arterial pressure

N-acetyl-aspartyl-taurine produces a significant dose-dependent hypotension from 50 mg/kg, which continues for 10 mins. (after the injection) with the doses of 100 and 200 mg/kg (37% of basic value).

Acetylaspartate and taurine produce a hypotension which is at maximum equal to 8% of the basal pressure. This hypotension is fleeting and never goes beyond the first minute of observation.

2. Cardiac frequency

N-acetylaspartyl-taurine and taurine induce a moderate initial bradycardia (<10% of basal frequency), whilst acetylaspartate is without effect.

3. Femoral flowrate

N-acetylaspartyl-taurine significantly increases the femoral flowrate:

+17% with 25 mg/kg
+62% with 100 mg/kg
+78% with 200 mg/kg

The variation is dose-dependent with N-acetylaspartyl-taurine, whilst taurine increases the femoral flowrate only at high doses and without dose-dependence.

Acetylaspartate does not raise the femoral flowrate.

The cardiac output and the vertebral flowrate are not modified in dose-dependent manner.

4. Vascular resistances

These resistances decrease significantly, beyond the first minute after administration, only with N-acetylaspartyl-taurine for which this effect is dose-dependent on the total resistance and the femoral resistance.

5. Systolic work

N-acetylaspartyl-taurine is without effect on the systolic work; taurine and especially acetylaspartate increase it significantly.

None of the products studied modifies the effects of noradrenaline.

In conclusion, it appears that N-acetylaspartyl-taurine induces a hypotension significantly greater than that provoked very fleetingly (of the order of one minute) by the other two products; this specificity of the action of N-acetylaspartyl-taurine is confirmed by the effects observed on the femoral flowrate.

The product according to the invention (N-acetylaspartyl-taurine) is useful in humans as active product in drugs with hypotensive and/or antihypertensive effect).

The product may be administered by the oral route at a rate of 0.5 to 1.5 g per day divided into one or more doses. The active agent may be administered in association with or mixed with a pharmaceutically acceptable non-toxic inert vehicle or excipient.

Of course, the product according to the invention, as expected, does not present any toxicity.

The following non-limiting Example illustrates the process for preparing N-acetylaspartyl-taurine.

EXAMPLE

Acylation of the taurine by N-acetyl-aspartic anhydride is effected according to the following scheme and technique:

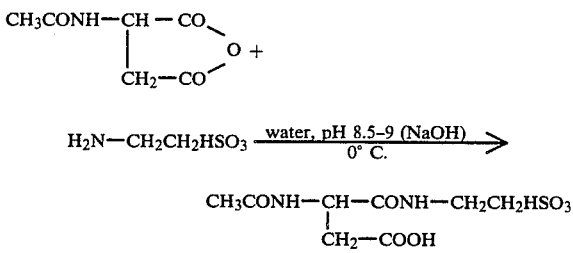

Dissolve 1.05 mole of taurine in 500 ml of water, adjusting the pH to 9.0 by addition of 10N caustic soda. Cool this solution to 0° C. then add, with vigorous stirring, 1 mole of N-acetyl-L-aspartic anhydride, in one hour, in small portions. (Keep this anhydride protected from humidity before addition). Stir for a further 10 mins. after the end of the addition. The pH is permanently measured and maintained between 8.5 and 9 by addition of a 4N sodium hydroxide solution.

The solution obtained is then percolated over sulfonic cationic resin (C-20 type, trademark "Duolite"). The percolate is concentrated in vacuo up to a volume of 400 ml. The syrup obtained crystallizes. The suspension is filtered after 24 hours of crystallization, washed with acetone, and dried. 0.65 mole of N-acetyl-L-aspartyl-taurine acid is obtained.

What is claimed is:

1. A process for treatment of hypertension in human or animal patients, which comprises administering an effective amount of N-acetyl-L-aspartyl taurine.

2. A process according to claim 1, wherein said N-acetyl-L-aspartyl taurine is administered orally.

3. A process according to claim 2, wherein said effective amount in humans comprises 0.5 to 1.5 g per day.

4. A process according to claim 1, wherein said N-acetyl-L-aspartyl taurine is administered in association with a pharmaceutically acceptable non-toxic inert vehicle or excipient.

* * * * *